United States Patent
Kane et al.

(10) Patent No.: US 6,955,876 B2
(45) Date of Patent: Oct. 18, 2005

(54) COMPOSITIONS AND SYSTEMS FOR IDENTIFYING AND COMPARING EXPRESSED GENES (MRNAS) IN EUKARYOTIC ORGANISMS

(76) Inventors: Michael D. Kane, 2619 Manchester Rd., Ann Arbor, MI (US) 48104; Aaron C. Nagel, 1575 Jay Ave., Ypsilanti, MI (US) 48198; Alan A. Dombkowski, 7300 Chichester, Canton, MI (US) 48187

(*) Notice: Subject to any disclaimer, the term of this patent is extended or adjusted under 35 U.S.C. 154(b) by 23 days.

(21) Appl. No.: 10/002,536

(22) Filed: Nov. 1, 2001

(65) Prior Publication Data

US 2003/0108874 A1 Jun. 12, 2003

(Under 37 CFR 1.47)

Related U.S. Application Data

(60) Provisional application No. 60/244,933, filed on Nov. 1, 2000.

(51) Int. Cl.[7] ............................ C12Q 1/68; C12P 19/34; C07H 21/04
(52) U.S. Cl. ................... 435/6; 435/91.1; 435/91.2; 536/23.1; 536/24.3; 536/24.33
(58) Field of Search ..................... 435/6, 91.1, 91.2, 435/91.21; 536/23.1, 24.3, 24.33

(56) References Cited

U.S. PATENT DOCUMENTS 5,914,229 A * 6/1999 Loewy ........................ 435/6
6,120,996 A 9/2000 Belyavsky et al. .......... 435/6
6,270,966 B1 * 8/2001 Weinstein et al. ........... 435/6

FOREIGN PATENT DOCUMENTS

| WO | WO 99/42610 | 8/1999 |
| WO | WO 00/40757 | 7/2000 |

OTHER PUBLICATIONS

Kohroki et al. A Novel Strategy for identifying differential gene expression: An improved method of differential display analysis. Biochemical and Biophysical Research communications, vol. 262, pp. 365–367, Aug. 1999.*

* cited by examiner

*Primary Examiner*—Kenneth R. Horlick
*Assistant Examiner*—Cynthia Wilder
(74) *Attorney, Agent, or Firm*—Rader, Fishman & Grauer PLLC; James F. Kamp, Esq.

(57) ABSTRACT

The invention comprises compositions and systems to identify and compare expressed genes in a given in vivo or in vitro RNA sample, as well as the relative difference in mRNA expression between two or more samples, where desired. Furthermore, the invention comprises compositions and systems to identify novel genes. The invention comprises, without limitation, one or more mRNA specific identimers for use in reverse transcription that themselves comprise an oligo-T nucleotide sequence (at the 5' end) linked to a nucleotide sequence VNx (at the 3' end) where the V nucleotide immediately adjacent to the oligo-T segment is not a T.

32 Claims, 4 Drawing Sheets

Analysis of fluorescence-labeled 3' cDNA fragments for size and abundance

SEQUENCE LISTING

<160> NUMBER OF SEQ ID NOS: 5

<210> SEQ ID NO 1
<211> LENGTH: 61
<212> TYPE: DNA
<213> ORGANISM: Artificial Sequence
<220> FEATURE:
<223> OTHER INFORMATION: This is a synthesized sequence.
<220> FEATURE:
<221> NAME/KEY: misc_feature
<222> LOCATION: (1)..(50)

-continued

```
<223> OTHER INFORMATION: The poly-T tail may have between 8 and 50
      residues.
<220> FEATURE:
<221> NAME/KEY: misc_feature
<222> LOCATION: (52)..(62)
<223> OTHER INFORMATION: The sequence may have between 3 and 10
      residues selected from a or c or g or t.

<400> SEQUENCE: 1
tttttttttt tttttttttt tttttttttt tttttttttt tttttttttt vnnnnnnnnn      60 n                                                                     61

<210> SEQ ID NO 2
<211> LENGTH: 25
<212> TYPE: DNA
<213> ORGANISM: Artificial Sequence
<220> FEATURE:
<223> OTHER INFORMATION: This is a synthesized sequence.
<220> FEATURE:
<221> NAME/KEY: misc_feature
<222> LOCATION: (23)..(25)
<223> OTHER INFORMATION: n may be selected from a or c or g or t.

<400> SEQUENCE: 2
tttttttttt tttttttttt tvnnn                                           25

<210> SEQ ID NO 3
<211> LENGTH: 24
<212> TYPE: DNA
<213> ORGANISM: Artificial Sequence
<220> FEATURE:
<223> OTHER INFORMATION: This is a synthesized sequence.

<400> SEQUENCE: 3
tttttttttt tttttttttt aaac                                            24

<210> SEQ ID NO 4
<211> LENGTH: 24
<212> TYPE: DNA
<213> ORGANISM: Artificial Sequence
<220> FEATURE:
<223> OTHER INFORMATION: This is a synthesized sequence.

<400> SEQUENCE: 4
gtttaaaaaa aaaaaaaaaa aaaa                                            24

<210> SEQ ID NO 5
<211> LENGTH: 25
<212> TYPE: DNA
<213> ORGANISM: Artificial Sequence
<220> FEATURE:
<223> OTHER INFORMATION: This is a synthesized sequence.

<400> SEQUENCE: 5
tttttttttt tttttttttt ggttt                                           25
```

COMPOSITIONS AND SYSTEMS FOR IDENTIFYING AND COMPARING EXPRESSED GENES (MRNAS) IN EUKARYOTIC ORGANISMS

CROSS-REFERENCE TO RELATED APPLICATION

This application claims priority based on U.S. provisional patent application No. 60/244,933 filed Nov. 1, 2000.

FIELD OF THE INVENTION

The present invention relates to the fields of genomic and proteomic analysis. In particular, the present invention relates to the field of gene expression analysis.

BACKGROUND OF THE INVENTION

With progress in sequencing many genomes, including among them the human genome, there is additional interest in understanding the significance of changes in gene expression. The ability to correlate changes in gene expression, for example, with specific treatments and phenotypes in clinical and non-clinical biological systems, allows scientists to understand the underlying cell biology and identify the roles of specific genes, receptors and signaling pathways. One objective, among many, of this research is to identify specific genes that may serve, for example, as biomarkers for disease progression or diagnostic criteria, as well as to identify gene expression products (e.g., proteins) that can be targeted as or by new therapeutic compounds in order to study, diagnose, prevent or cure disease.

There have been significant advancements in the human genome-sequencing project and in similar sequencing efforts that involve organisms of interest to basic and preclinical research, genetics, and agronomics. This progress has generated and continues to generate deoxyribonucleic acid ("DNA") and ribonucleic acid ("RNA") sequence databases that serve as informational resources and support advancement in the methods by which genomic and proteomic research is carried out.

However, current genomic tools and techniques continue to require significant known genomic sequence information for the organism or tissue under investigation, or require that the investigators derive libraries of clones from the particular organism or tissue. In order to build a DNA microarray that represents essentially all genes for a particular species under investigation (e.g., human), the investigating scientist must expend tremendous resources to identify all possible messenger RNAs ("mRNAs") that may be present in the studied sample. For example, high-density DNA microarrays, using large numbers of known genes, are required to conduct mRNA expression profiling in such samples. By comparison, use of low-density DNA microarrays creates a higher probability of "missing" genes (by omission from the array) that may be relevant to a given experimental paradigm.

Alternative methods, such as differential display and serial analysis of gene expression, may permit detection of differences in mRNA species between or among RNA samples. However, these methods also require significant resources to identify expressed genes and related expression products, such as mRNAs. For example, in order to identify differences in specific genes using differential display, segregated bands must be removed (excised) from an electrophoresis gel, amplified using polymerase chain reaction ("PCR") techniques, and then sequenced. Similarly, serial analysis of gene expression ("SAGE") requires significant sequencing resources to identify any differences in known and unknown genes.

The present invention addresses limitations in the prior art by comprising compositions and systems that incorporate novel strategies whereby molecular or biochemical assay compositions and systems are linked to DNA or RNA sequence databases for optimal resource efficiency in assaying gene expression.

SUMMARY OF THE INVENTION

The invention comprises compositions and systems to identify any or all genes expressed in a given in vivo or in vitro RNA sample, as well as the relative differences in mRNA between two or more samples, where desired. Furthermore, the invention comprises compositions and systems to identify novel genes (expressed as mRNA), by way of one example only, by detecting mRNA 3' end fragments that do not correspond to any known sequence. Thus, embodiments of the invention (1) may identify any or all genes (mRNAs) expressed in a given eukaryotic sample, (2) support discovery of novel genes, or (3) may identify mRNAs that are expressed at different levels between two or more samples. The invention further comprises custom microarray design and production where genes shown to be present and/or differentially regulated between two samples can be used to produce project- or disease-specific microarrays that detect the genes of interest. Moreover, embodiments of the invention comprise systems of nucleic acid fragment collection and analysis.

The invention comprises compositions and systems to identify the relative expression level of any or all eukaryotic mRNAs in one or more samples. The invention comprises, without limitation, one or more mRNA specific primers for use in reverse transcription that themselves comprises an oligo-dT nucleotide sequence (at the 5' end) linked to a nucleotide sequence (at the 3' end) where the nucleotide immediately adjacent to the oligo-dT segment is not a T. This sequence can be written (from 5' to 3' end) as Tn-VNx, where n=any integer of 8 or greater describing how many T nucleotides are present; V=nucleotides A, G, or C; each N=nucleotides A, G, C, or T, and x=any integer 3 or greater that describes how many N nucleotides are present (SEQ ID NO: 1). (For purposes of the invention, the designation "d", or "deoxy", shall also include the "nondeoxy" form where appropriate as known by those of ordinary skill). The complete primer (oligo-dT region+VNx sequence) of the invention is called an "identimer."

Embodiments of the invention may employ different or every combination of the Tn-VNx sequence. The 5' end of the identimer comprises a reporter marker or molecule, by way of example only and without limitation, a fluorescent molecule, which allows detection of the resulting fragment. The Tn-VNx sequence of the invention includes priming of all genes containing the complementary sequence at the 3' end (immediately adjacent to the poly-adenylation tail), providing information about the gene's identity (i.e. the mRNA's sequence at the 3' end), limiting the number of reaction products to a useful number, and enabling detection of the resulting 3' end fragment, as one example only, by fluorescence detection.

After deriving double-stranded complementary DNA ("cDNA") in the invention, one or more 3' end fragments are generated by a sequence-specific cleavage of the double-stranded cDNA, for example, by restriction endonuclease cleavage or other sequence-specific cleaving agents known to those of ordinary skill. The invention generates 3' end fragments of cDNA where the 5' end is known (complementary to the VNx nucleotide sequence), the 3' end is known (e.g., the restriction endonuclease recognition sequence), and the size is known (by way of one example only, from electrophoretic separation or reverse HPLC). In some embodiments, the resulting data is accumulated, analyzed, and stored in a database. The resulting data permits identification of expressed mRNA in a single sample, or, by comparing the abundance of fragments from a control sample to a test (or unknown) sample, the relative differences in expression of genes of interest may be determined among samples.

The invention allows research and clinical scientists to identify any or all genes expressed in a given in vivo or in vitro RNA sample, as well as the relative differences in mRNA between two or more samples, where desired. Furthermore, novel gene (mRNA) discovery is made possible since mRNA 3' end fragments can be identified that do not correspond to any known sequence.

DETAILED DESCRIPTION OF THE PREFERRED EMBODIMENTS

Figure 1:
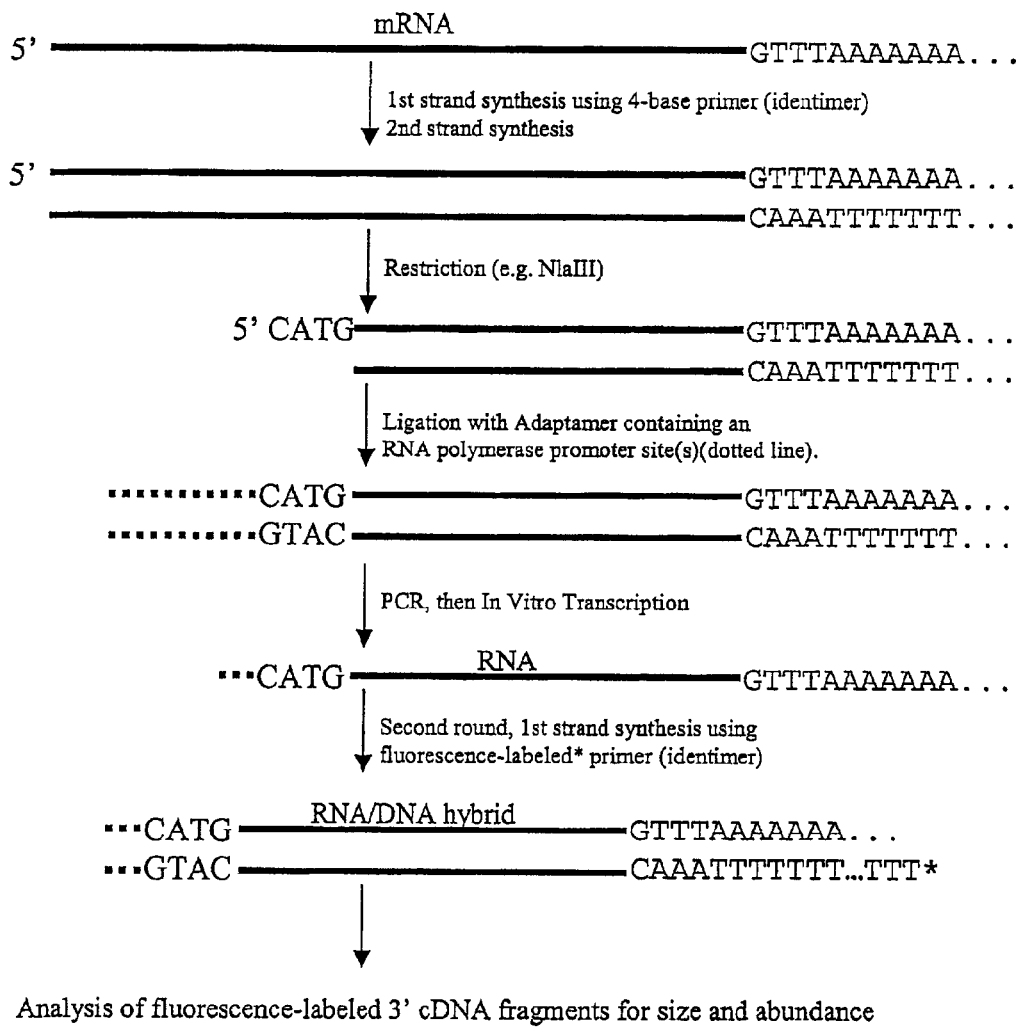
FIG. 1 shows a schematic diagram of one embodiment of the invention which generates 3' cDNA fragments for the assay of poly-adenylated mRNAs in eukaryotic samples.

As is commonly known, transcription is the transfer of the genetic information from a host's archival copy of DNA to mRNA. In typical transcription, RNA polymerase binds to a particular region of archival DNA and begins to make a strand of mRNA with a base sequence complementary to the DNA template that is "downstream" of the RNA polymerase binding site. When this transcription is finished, the portion of the DNA that coded for a protein, i.e., a gene, is now represented by an mRNA molecule that can be used as a template for translation into gene products, such as proteins. Thus, levels of gene expression can be evaluated by identifying and characterizing the mRNA complement of a host.

Those of ordinary skill will also appreciate that, to further evaluate the levels of gene expression, polyA mRNA may be prepared from the desired organism or tissue, and the first strand of cDNA may be synthesized from the mRNA template using, as some examples only, an RNA-dependent DNA polymerase, such as reverse transcriptase, and an oligonucleotide primer. A second strand of cDNA may be synthesized by one of the methods known to one of ordinary skill in the art, for example, by replacement synthesis or by primed synthesis. The resulting cDNA strands are thus available for further analysis and characterization.

With this background in mind, the invention comprises an identimer with three or more nucleotides upstream of a poly-T tail, combined with a restriction enzyme that cleaves ds DNA in a sequence-specific fashion, to generate 3-prime end cDNA fragments of expressed genes. The expression level of a given gene is proportional to and correlates with the amount or abundance of tho respective 3' cDNA fragment level. Genes (expressed as mRNAs) arc identified by combining the known sequence of 3 or more nucleotides immediately adjacent to the poly-A tail (complementary to the Nx base-anchored primer)(SEQ ID NO: 1), the specific DNA sequence recognized or cut by the restriction enzyme(s) employed, and the size of the 3' fragment. The size of the 3' fragment represents the distance between the Nx base-anchored priming (poly-adenylation site) and the nearest restriction enzyme cut site. The identity of the mRNA (gene) may be derived by searching an mRNA or DNA database for the nucleotide sequence that matches the N(x)-base priming site, the restriction enzyme cut site, and the distance between the printing site and the cut site. Ambiguous calls are avoided by repeating the protocol with one or more restriction enzymes that recognize or cut a different nucleic acid sequence.

In one embodiment, without limitation, the invention comprises up to 192 different identimers that represent all combinations of the primer designated as 5' Tn-VNNN 3' (n=an integer of preferably 21 representing the number of T's; V=nucleotides A, G, or C but not T; each N=nucleotide A, G, C, or T)(SEQ ID NO: 2), which is designed to identify the 4 nucleotides immediately adjacent to the poly-adenylation site in eukaryotic mRNA. The Tn or poly-dT in the identimer is designed to anneal to the poly-A tail in eukaryotic mRNA. In one embodiment, without limitation, more than one set of 192 identimers (the permutations of VNNN=3×4×4×4) is employed, and each set is used with a single RNA sample. These identimer sets, and thus the samples, are differentiated by adding a distinct, detectable molecular label or marker, by way of one example only, a fluorescent label, to the 5' end of each identimer in a set, with all identimers within a set having a similar 5' marker. The identimer is annealed to mRNA using buffer and temperature conditions that are known in the art for optimal sequence-specific priming, and reverse transcription is carried out. Second-strand synthesis is subsequently carried out to produce double-stranded ("ds") cDNA that is amenable to restriction enzyme cleavage. Enzyme-mediated, sequence-specific cleavage is carried out, resulting in fragmented ds cDNA. For each set where different cleavage enzymes or agents are used, the invention will generate different 3' end fragments for characterization. In this manner, the invention generates and analyzes cDNA fragments that are assayed for size (e.g., mobility in a gel) and amount.

In one embodiment, without limitation, the invention generates 3' cDNA fragments where the 4 nucleotides immediately adjacent to the poly-adenylated tail (VNNN) are known, the sequence-specific location (i.e., restriction site) is known, and the size of the fragment is determined and used to establish the distance between the restriction site and the poly-adenylated tail. The amount of the cDNA fragment, as well as the sample it represents, is determined by assaying the signal intensity of the 5' label on the employed identimer set by means known to those of ordinary skill in the art. Differences in the normalized intensity of the 5' labels for a specific cDNA fragment indicate differences in the respective mRNA among or between the RNA sample sets under investigation. Information regarding the identity of an expressed mRNA is derived from knowing the 4 nucleotides immediately adjacent to the poly-adenylated tail, the nucleotide sequence for the restriction site employed, and the distance between the poly-adenylated tail and the restriction site nearest to the poly-adenylation site with respect to the primary nucleic acid sequence (i.e., the most 3' restriction site in the mRNA sequence).

In another embodiment, without limitation, samples representing control and one or more experimental samples of mRNA may each be divided into 192 aliqouts, with one identimer of the 192 identimers added to each respective aliquots. The respective identimer sets may contain different distinct, detectable molecular labels or markers on the 5' end of each identimer in a set, with all identimers within a set having a similar 5' label. Reverse transcription and second strand synthesis is similarly conducted according to means known to those of ordinary skill in the art to produce ds cDNA that is amenable to restriction enzyme cleavage. Enzyme-mediated, sequence-specific cleavage is carried out, resulting in fragmented ds cDNA. Comparison of fragmented ds cDNA corresponding to each respective identimer yields data showing the relative expression of the corresponding gene between control and test samples. One of ordinary skill will appreciate that other useful embodiments are apparent, as some examples only, by varying the type and number of markers in each identimer set, as well as by varying the sequence-specific cleavage enzymes used to produce fragmented ds cDNA.

In one embodiment, without limitation, the invention comprises a system that compares two or more RNA samples resulting in (1) cDNA fragments of essentially all mRNAs (genes) present in the samples, (2) identifies the subset of genes that are different between the samples, and (3) provides immediate sequence information to identify known genes from the cDNA fragments. This invention thus has significant advantages over existing art because prior sequence information or clone library construction is not needed to enable the assay, as in the case of DNA microarrays that require significant resources to produce the DNA microarray. Instead, the invention provides immediate sequence information, in addition to information concerning changes or differences in mRNA level, to determine mRNA expression level and mRNA identification in one assay. Furthermore, the invention generates cDNA fragments from all mRNAs present in the sample for subsequent investigation by common molecular biology techniques such as cloning, PCR, sequencing, etc. It is important to note that the invention does not require prior knowledge of the sequence of the genome of the organism under investigation and can be employed in organisms that lack significant genomic sequence information. Thus by identifying specific differences in mRNAs levels, critical changes in gene activity relevant to the research or disease model under study can be derived where little or no genomic sequence information is available. In this paradigm, preliminary information can be utilized to direct selective cloning and sequencing efforts, as well as to produce a DNA microarray specific to the relevant mRNAs for a more exhaustive, high throughput study across many samples in the research or disease model under investigation.

The determination of the size and abundance of 3' cDNA fragments requires labeling the fragments with a detectable marker entity or grouping. In one embodiment of the invention, without limitation, labeling the 3' cDNA fragments involves fluorescence. By way of one example only, a sample derived from a biological reference or control group is labeled with one fluorescent molecule or group, and a sample derived from a biological test or study group is labeled with a different fluorescent molecule or group. The detection method of the invention comprises a fluorescence detector that can identify and distinguish the fluorescent molecules or groups employed during labeling. One method of labeling involves the addition of one or more fluorescent groups to the identimer, preferably at the 5' end of the identimer to avoid interfering with reverse transcription priming. Another labeling method, among others, uses fluorescence-modified reverse transcription substrates (e.g., fluorescence-modified trinucleotides) that are added to the reverse transcription reaction and incorporated into the cDNA during reverse transcription.

FIG. 1 shows a molecular protocol of one embodiment of the invention to generate 3' cDNA fragments for the assay of all poly-adenylated mRNAs in eukaryotic samples. The sample under investigation is divided into 192 aliquots, and first strand synthesis (reverse transcription) is carried out using all VNNN combinations of the identimer, followed by second strand synthesis. The ds cDNA is cleaved in a sequence-specific manner using a restriction enzyme that involves a 4-base recognition sequence (e.g., NlaIII). The resulting fragments are ligated to an adaptamer that contains one or more RNA polymerase promoter sites for subsequent in vitro transcription. The 3' cDNA fragments are initially enriched using PCR, primed at the adaptamer and the poly-adenylation site (i.e. identimer), and subsequently employed as a template for in vitro transcription promoted within the adaptamer (e.g. T7 polymerase promoter in the ligated adaptamer). This results in an amplification of the sequence adjacent to, and downstream from, the RNA polymerase promoter sequence, which includes the restriction site and the poly-adenylation site. "Second round" first strand synthesis is carried out using a fluorescence-labeled primer (identimer) to enable the detection of all 3' cDNA fragments for size and abundance (fluorescence label is denoted as an "*" at the 5' end of the identimer in FIG. 1). The entire process is repeated using a different restriction enzyme that employs a different recognition sequence (e.g. MboI). Gene (mRNA) identification is made by collecting knowledge of the 4 nucleotides upstream of the poly-adenylation site (determined by identimer priming), the sequence of the restriction enzyme recognition site, and the size of the fragment that provides the distance between the poly-adenylation site and the proximal restriction site. This information is employed to search the known sequence database(s) to identify the mRNA(s) that match these criteria.

In some embodiments, the identification of a gene or mRNA utilizes information derived from the identimer sequence, the restriction enzyme recognition sequence(s), and the size of the resulting cDNA fragments. This information is then employed to search an mRNA sequence database to identify the specific genes or mRNAs in the samples under investigation. The data used to search the mRNA database are derived by means of the invention. The mRNA nucleotide sequence of the bases immediately adjacent to the poly-A tail are derived from knowledge of the complementary identimer sequence. For example, if the identimer for a given reaction has the sequence 5'-TTTTTTTTTTTTTTTTTTTTAAAC-3' (SEQ ID NO: 3), then any mRNAs identified from this reaction will contain the sequence 5'-GTTTAAAAAAAAAAAAAAAAAAAA-3' (SEQ ID NO: 4). Further information is derived from the determination of the length of labeled cDNA fragments and the restriction enzyme employed to generate the fragments. For example, if the first restriction digest of the identimer reaction above employs the restriction enzyme NlaIII, which cuts at the sequence 5'-CATG-'3, then a cDNA fragment that is 334 bases in length identifies and mRNA sequence that contains the 5'-CATG-'3 sequence 314 bases from the poly-adenylation site. This take into account the 20 "T" bases on the identimer (i.e. 334−20=314). If the second restriction digest of the identimer reaction employs the restriction enzyme MboI, which cuts at the sequence 5'-GATC-3', then a cDNA fragment that is 889 bases in length identifies an mRNA sequence that contains the 5'-GATC-5' sequence 869 bases from the poly-adenylation sequence. Using this information to search an appropriate database, one can identify the mRNA as human precerebellin (GI# 180250), which matches the analytical data. If no mRNA is present in the database, then one can employ a similar bioinformatical strategy to predict the identity of the unknown mRNA or approximate the identity of mRNA or gene family involved. Similarly, if the samples are derived from an organism that lacks an adequate mRNA or gene sequence database, the mRNA is identified using the database from a closely related species.

In some embodiments, the invention comprises an in vitro transcription step for optimal sensitivity. Each reaction employs one or more primed reverse transcription step resulting in an mRNA:cDNA hybrid. The mRNA:cDNA hybrid is converted to ds cDNA using a "second strand" reaction that may involve, as examples only, RNase H, a DNA polymerase, and a DNA ligase. Subsequently the ds cDNA is fragmented using one or more restriction enzymes or other cleaving agents that cleave DNA in a sequence-dependent fashion. Subsequently a specific DNA sequence, or "adaptamer", containing one or more RNA polymerase promoters, is ligated onto the restriction site, allowing in vitro transcription-mediated amplification of the adaptamer-ligated fragments. The resulting RNA sequences include a 3' poly-A tail and serve as a template for identimer-primed reverse transcription that produces 3' cDNA fragments. These fragments, which may correspond to cleaved fragments, are flanked by known sequences from the identimer hybridization site and restriction site, and the fragments can be analyzed for size and abundance to determine the identity of the mRNA and the expression level in the sample, respectively.

In one embodiment of the invention, without limitation, identification of the gene associated with a given mRNA fragment, observed as a gel band or chromatographic mobility peak, is attained by an automated matching of the fragment length, restriction enzyme(s), and the known VNx recognition sequence to all predicted fragments obtained in a computational analysis of an mRNA database. A representative set of mRNA sequences for the organism under investigation is submitted to a computational analysis that, for each sequence, identifies the start of the poly-adenylation (polyA) site, the VNx sequence immediately upstream of the polyA site (recognition sequence), and the location of all restriction sites that would be subject to cleavage by the restriction enzymes used in the biochemical protocol. For each restriction enzyme used, the cleavage site upstream and proximal to the mRNA 3' end is identified. The predicted fragment length is calculated by counting the number of nucleotides from the proximal cleavage site to the beginning of the polyA site and adding the number of nucleotides for the length of the oligo-T portion of the identimer primer. Thus, for each mRNA sequence in the representative database, an algorithm may predict the fragment lengths that would be observed if the given mRNA sequence were present in the sample and analyzed with the biochemical protocol. A computer application calculates all predicted fragments for a specified set of restriction enzymes and four-base recognition elements. To associate a gene with a fragment obtained in the biochemical protocol (the "target fragment"), the target fragment is compared to all predicted fragments. Predicted fragments matching the target fragment length, restriction site, and VNx recognition sequence are putative matches. An unambiguous identification is obtained when only one predicted fragment matches the target fragment. Gene identification is accomplished by referring to the sequence information associated with the predicted fragment. In the case where the target fragment matches multiple predicted fragments (multiple genes), the use of additional restriction enzymes provides an unambiguous identification. In such a case, identification requires that all predicted fragments for the putative gene must match target fragments observed in the experiment. In other words, each restriction enzyme may produce an observed fragment for the given gene; when each of these target fragments is matched to predicted fragments from a single gene then identification of the target fragments can be made.

In some embodiments, the invention comprises providing a transcript (mRNA) sequence database for the organism under investigation, as well as an executable program to mine and match the database with the 3' cDNA fragments.

Determining relative differences between two different RNA samples involves comparing the abundance of all 3' fragments, which have been differentially labeled for detection. For example, a comparative increase in the signal intensity of a specific 3' cDNA fragment(s) indicates the mRNA that gave rise to the fragment(s) is more abundant in the respective sample. Furthermore, the appearance or disappearance of a specific 3' cDNA fragment(s) indicates induction or repression, respectively, of the mRNA that gave rise to the fragment(s).

EXAMPLES

The following examples illustrate embodiments of the invention but in no way restrict the overall scope of the invention to only those described below.

Example 1

First and second strand cDNA synthesis. First strand synthesis is performed by means known to those of ordinary skill (using any experimental cell/tissue type) on the total RNA population utilizing a four-base identimer of sequence NNNVT$_{21}$, where each N=A, C, T, or G, and V=A, C, or G but not T (SEQ ID NO: 2). In practical application, the total number of unique identimer tags theoretically required to span the total estimated mRNA population (in a eukaryotic organism) would be 192 (thus 192 unique subsets). Compared with most differential display protocols, which typically utilize a two-base anchored primer for first strand synthesis, a four-based identimer has advantages by: (1) significantly reducing the complexity of the mRNA pool by a factor of 16 (192/12=~16), thereby reducing the number of bands displayed per fingerprint (or subset); (2) providing a more accurate prediction of the candidate mRNA(s) of interest through the additional two nucleotide sequence at the 3'-end of each mRNA preceding the poly-A (along with restriction site); and (3) allowing for more stringent annealing temperature (e.g., 50° C.), thereby reducing potential mispriming during first strand synthesis. Following first strand synthesis, ds cDNA 5' was synthesized using a cocktail of requisite enzymes (DNA Polymerase I, RNase H, and E. coli DNA ligase), for example, according to the method of Gubler and Hoffman (Life Technologies Instruction and Technical manuals).

Restriction enzyme digestion. Following second strand synthesis, ds cDNAs are digested separately with any four-base recognition sequence—specific class IIS restriction enzymes, yielding a 4-base cohesive or recessive end, ideal for improving the efficiency of subsequent ligation reactions. Assuming the average size of a synthesized cDNA is approximately 1200 base pairs ("bp"), the 4-base recognition enzyme will cut once every 256 bp (on average), generating 5 different fragments (on average). However, the fragment of interest is the most 3' fragment, which is selected for in subsequent steps.

RNA polymerase—specific adaptor ligations. An extended ds promoter recognition sequence specific for the respective RNA polymerase of choice (e.g. T7) is ligated (using a standard T4 DNA ligase protocol) to the 5' protruding region at the 3' end of each ds cDNA containing the four-base cut site. The RNA polymerase adaptor has an extended complementary sequence to the cohesive or recessive end generated by each respective enzyme. All cDNAs now acquire a universal promoter site (and primer site) specific for the RNA polymerase employed.

Selective PCR amplification of 3'—cDNA fragments. Ligation products are subjected to a selective PCR amplification of the representative 3'—cDNA pools by known means, using a sense strand specific primer derived from the RNA polymerase—specific ds adaptor and each individual identimer tag(s) originally used for first strand synthesis. This step selectively amplifies the most 3' ds fragments that are flanked by the adaptor sequence ("forward primer annealing site") and the poly-A site ("reverse primer" or "identimer annealing" site). PCR amplifications were performed using a HotStar™ Taq master mix (Qiagen, Valencia, Calif., USA) in a 30 μl reaction format as follows: 2.5 U HotStar Taq™ DNA Polymerase (Qiagen); 1×PCR buffer; 200 μM dNTPs; 0.02 μM identimer tag; 1.0 μM T3 sense primer. The PCR conditions were as follows: initial activation and denaturing step at 95° C. for 15 min followed by 25 cycles at 94° C. for 30 sec, 50° C. for 1 min, 72° C. for 1 min with a final extension step for 5 min at 72° C. 3' PCR fragments are purified from residual reaction components, quantified, and used for proceeding reactions.

Selective linear amplification of 3' PCR pools. Another drawback to most current differential display—derived methods is the underrepresentation of the mRNA pool due to differential display's preferential bias toward high copy number mRNAs. Given that the percentage of low to rare abundance mRNAs can comprise up to 90% of the total mRNA pool, alternative or extended strategies (following PCR) can be employed to obtain more accurate representation of all expressed mRNAs. This entails a linear amplification event (i.e., in vitro transcription) following an exponential amplification event (PCR) as a non-biased approach to further analyzing those messages that otherwise would not be observed following PCR.

Each PCR reaction (containing a representative 3' pool based on the identimer used) is subjected to an in vitro transcription reaction using the RNA polymerase of interest for the appropriate time interval using the following reaction components (final concentration): 1–2 μg template DNA; 7.5 mM of each individual nucleotide; 10 mM DTT; 1× reaction buffer; RNA polymerase. Following linear amplification, in vitro transcribed mRNAs are purified, quantified, and used for a second-round first strand synthesis, respective to the first step in this overall method.

Figure 2:
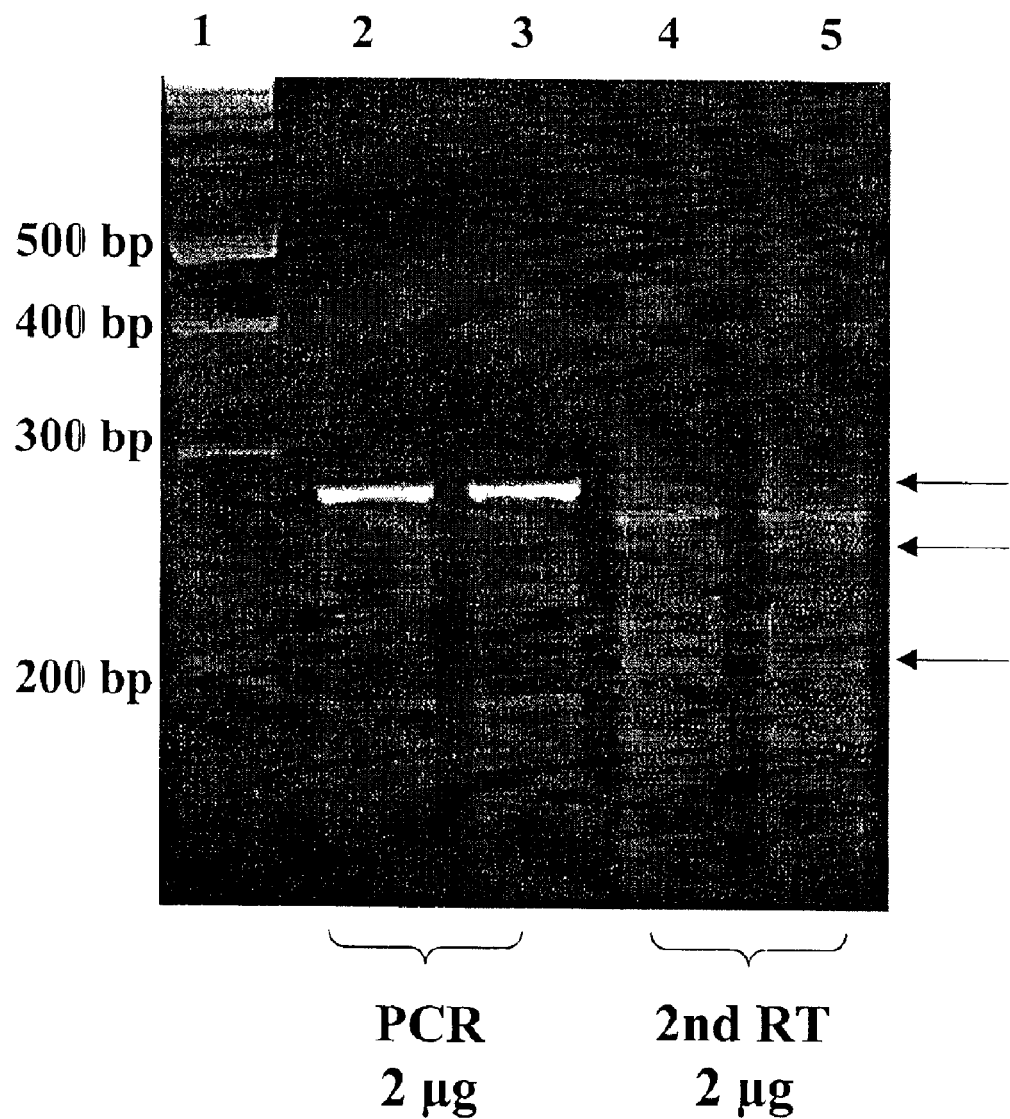
FIG. 2 shows a comparative fingerprint analysis between PCR amplified samples by an existing method and by the invention using an intermediate linear amplification step.

FIG. 2 shows a comparative fingerprint analysis between PCR amplified samples using an existing approach and the invention's intermediate linear amplification step. The samples are: Lane 1, 100 bp ladder; Lane 2, 2 μg 'control' PCR fingerprint; Lane 3, 2 μg 'treated' PCR fingerprint; Lane 4, 2 μg 'control' RT product; Lane 5, 2 μg 'treated' RT product. Control and treated samples represent total RNA samples from untreated and etoposide-induced apoptosis in HEK293 cell cultures, respectively. The arrows in FIG. 2 indicate unique bands displayed using the invention's linear amplification step for comparing expression profiles, which would otherwise not be detected using current art. Differences in migration patterns between PCR fingerprints and RT fingerprints are attributed to the RNA polymerase recognition site ligated into the fragments, which are not transcribed during in vitro transcription in the system of the invention.

Second-round first strand synthesis and display of fingerprints.

In vitro transcribed mRNAs are subjected to a second-round first strand synthesis reaction by ordinary means in order to generate a double-stranded mRNA:cDNA duplex. Experimental samples are end-labeled using 5'-fluorescence-labeled identimer tags (i.e., control sample, cy-3; treated sample, cy-5). Following synthesis, 3' fingerprints are analyzed for differences in expression levels using denaturing high-performance liquid chromatography (DHPLC) or gel electrophoresis. All detectable fragments are analyzed for abundance and subsequently employed for gene (mRNA) identification by a bioinformatic method that employs the identimer sequence, the restriction site, and the length of the fragments. Fragments can be collected for subsequent applications or investigation such as DNA microarray production, sequencing, cloning, etc.

Figure 3:
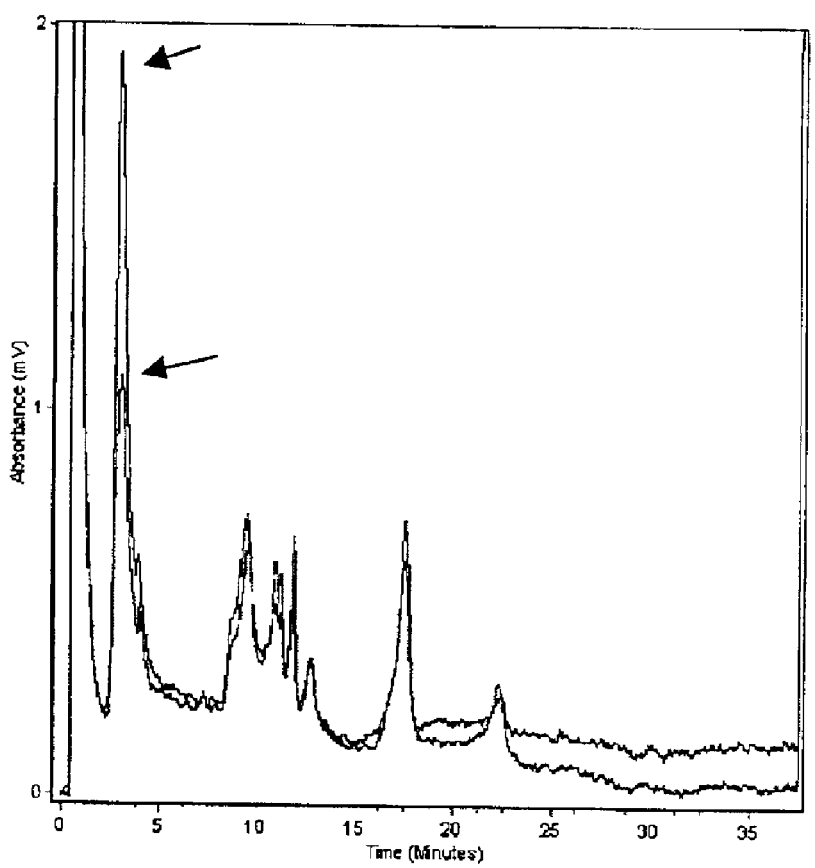
FIG. 3 shows a reverse phase HPLC separation of control and treated samples showing a 3' cDNA fragment of similar size but different abundance, indicating a difference in expression level for a specific mRNA between the samples.

FIG. 3 shows an example of reverse phase HPLC separation of control and treated samples. The results showing a 3' cDNA fragment (arrows) of similar size but different abundance, indicating a difference in expression level for a specific mRNA between the samples. Note that all other peaks (bands) in the trace co-migrate and are at the same abundance (based on peak height), indicating these 3' cDNA fragments are derived from mRNAs that are present in both samples at the same expression level. Control and treated samples represent total RNA samples from untreated and etoposide-induced apoptosis in HEK293 cell cultures, respectively.

Example 2

In one embodiment, the invention is a system whereby the identity and relative expression level of all eukaryotic mRNAs (messenger RNAs) are determined. Some components of the invention include, without limitation (1) primer design & reverse transcription, (2) production of double-stranded cDNA, (3) sequence-specific cleavage of ds cDNA, and (4) fragment detection & analysis.

Primer Design. The invention takes advantage of the polyadenylation of eukaryotic mRNAs by utilizing an anchored oligo-T primer. The basic primer design includes an oligo-T nucleotide sequence (5' end) linked to a 5-nucleotide sequence (3' end) where the bases immediately adjacent to the oligo-T stretch is not a T. This sequence can be written (5' to 3') as Tn-VNNNN (n=any single integer of 8 or greater representing how many T bases are present). The 5' end of the primer contains one or more reporter molecules or markers (e.g. fluorescent molecule, hapten, biotin, radioisotope, etc.) that allows for detection of the resulting fragment (e.g. size determination) and enables collection of the resulting fragment if desired. Every combination of the VNNNN sequence is employed (in this case, 768 combinations) and occasional modifications in length are utilized to accommodate common vs. rate 3' end sequences. The 768 combinations (i.e. reactions) are managed by employing multi-well plates (e.g. 384-well plate) and multiple reporter molecules (e.g. two reactions per well in a 384-well plate using two different fluorescent reporter molecules). The Tn-VNNNN sequence comprises priming of all genes containing the complementary sequence at the 3' end (immediately adjacent to the poly-adenylation tail), providing information about the genes identity (i.e. the mRNA's sequence at the 3' end), and enabling detection of the resulting 3' end fragment (e.g. fluorescence detection). The VNNNN sequence primer (including the oligo-T region) is called the "identimer" and the complementary sequence (i.e. mRNA sequence) to the 5 (non-oligo-T region) nucleotides of the identimer sequence is called the "identifier" sequence (which utilizes DNA sequence nomenclature rather than RNA; T rather than U). The "identifier" sequence is used in identifying the specific mRNA in a sequence database, along with the 3' fragment size and restriction enzyme recognition sequence.

Reverse Transcription. Reverse transcription ("RT") is a molecular biology protocol known to those of ordinary skill that allows a complementary DNA sequence to be synthesized using an RNA template. Many enzymes are available to carry out this reaction, which involves adding nucleotides to the 3' end of the primer or growing DNA strand. A result of RT is a RNA-DNA heteroduplex. Since the identimer primer utilizes the poly-A tail on eukaryotic mRNAs, almost all RNA will be employed for RT. The basic premise involves annealing the identimer primer to the RNA that enables RT.

Production of Double-Stranded cDNA. Once the RT reaction is complete, ds-cDNA is generated by any method utilized by those of ordinary skill in the art. This protocol known to those of ordinary skill may employ, for example, RNAse H to produce nicks and gaps in the RNA strand on the RNA-DNA heteroduplex while simultaneously employing DNA polymerase I, as well as DNA ligase, to replace the RNA strand with "second strand" DNA.

Sequence-Specific cleavage of Double-Stranded cDNA. After deriving ds cDNA, one or more 3' end fragments are generated by a sequence-specific cleavage of the ds DNA. One embodiment, among others, would involve using a restriction enzyme ("RE") that includes a 4 base recognition sequence. The average length of the cut fragments may be estimated at 256 bases using a RE with a 4-base recognition sequence. Furthermore, the RE recognition sequence provides the 5' end sequence information on the fragment generated (i.e. the RE recognition sequence itself). The resulting fragments can be ligated to a common primer for amplification if desired.

Fragment Detection & Analysis. The previous steps generate 3' end fragments where the identimer sequence and the RE recognition sequence are known. Determining the size of the fragment in the system (as one example, by capillary electrophoresis) provides information about the location of the RE recognition sequence and enables analysis of the fragment information with the appropriate database. This creates a novel and desirable data set describing the mRNA expression profile(s) of RNA isolated from any eukaryotic samples or model system. Furthermore, collection of these fragments for sequencing may be utilized for identifying novel sequences.

Figure 4:
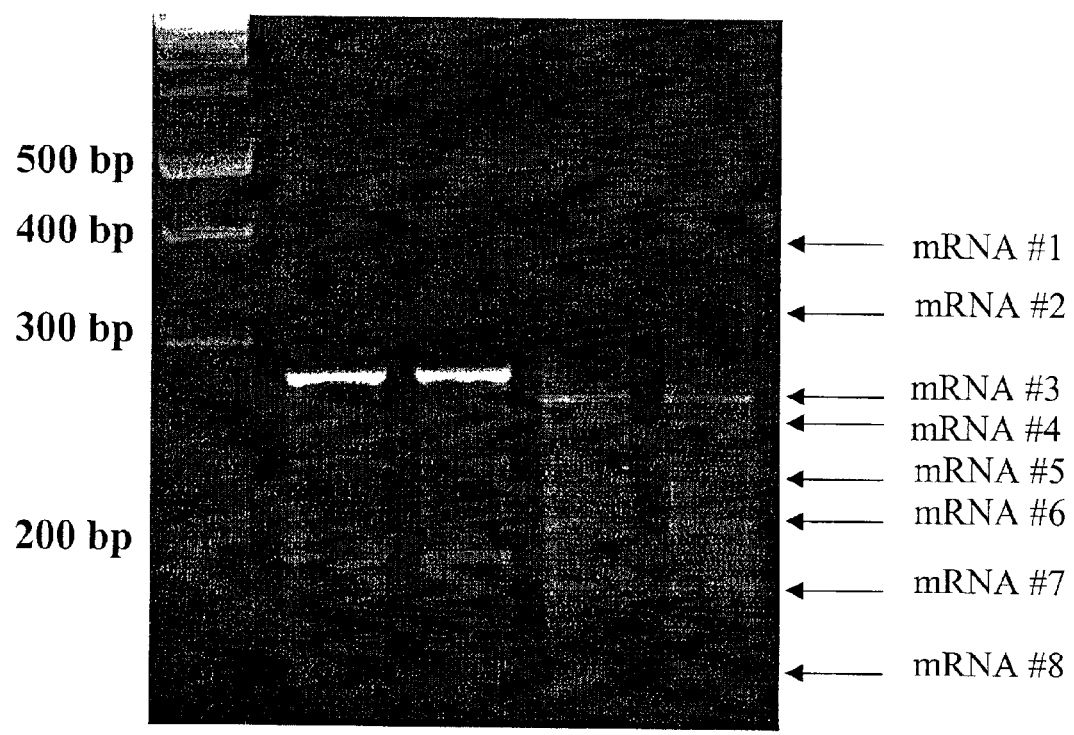
FIG. 4 shows the identification of mRNA in a test sample from cDNA fragments.

FIG. 4 shows the identification of mRNA in an HEK 293 test sample from cDNA fragments. The identity of the specific mRNAs has been established from combining the specific VNNNN identimer used in the experiment (5' TTTTTTTTTTTTTTTTTTTTGGTT 3' (SEQ ID NO: 5)), the specific restriction enzyme employed (NlaIII, cut Site is 5' CATG 3'), and the size of the fragments from the gel. Using this information, a search of publicly available mRNA and DNA sequence databases produced the results for the samples shown in Table 1:

TABLE 1

| Band | Size (bp) | GenBank ID | Gene/mRNA Description |
| --- | --- | --- | --- |
| 1 | 380 | 5102748 | Homo Sapiens mRNA full length insert cDNA clone EUROIMAGE 35971 |
| 2 | 315 | 180250 | Human precerebellin and cerebellin mRNA, complete cds |
| 3 | 275 | 5102752 | Homo Sapiens mRNA full length cDNA clone EUROIIMAGE 609395 |
| 4 | 250 | No ID | No matching mRNA sequence |
| 5 | 220 | No ID | No matching mRNA sequence |
| 6 | 200 | No ID | No matching mRNA sequence |
| 7 | 155 | 6807752 | Homo Sapiens mRNA:cDNA DKFZp434L1016 |
| 8 | 120 | 3366801 | Homo Sapiens orphan G protein-coupled receptor HG38 mRNA, complete cds |

Preferred embodiments of the present Invention have been disclosed. A person of ordinary skill in the art would realize, however, that certain modifications would come within the teachings of the invention, and the following claims should be studied to determine the true scope and content of the invention. In addition, the methods and structures of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive.

What is claimed is:

1. A method for identification and characterization of gene expression in one or more samples, comprised of:
   (a) providing one or more samples comprising one or more mRNA molecules;
   (b) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a detectable marker at its 5' end;
   (c) contacting said mRNA with said identimer such that the polyT portion of the identimer hybridizes to the polyA tail of the mRNA and the VNx portion of the identimer hybridizes with portions of the mRNA immediately upstream of the polyA tail;
   (d) reverse transcribing the mRNA to produce a first strand cDNA that includes the identimer;

(e) synthesizing a second DNA strand complementary to the first strand cDNA to form a duplex;

(f) cleaving the duplex with at least one sequence-specific cleaving agent to provide one or more duplex cleavage fragments;

(g) ligating an adaptamer comprising an RNA polymerase promoter site to one or more of said cleavage fragments; and (h) amplifying the one or more ligated cleavage fragments using the identimer to produce one or more amplified fragments comprising sequences complementary to a 3' end of the mRNA.

2. A method of claim 1, further comprising the identification and characterization of the cleavage fragments according to the presence of the marker, the sequences corresponding to the VNx nucleotide sequence and the sequence associated with the sequence-specific cleaving agent, and the size of the fragment.

3. A method of claim 2, further comprising the identification of any gene associated with the cleavage fragments by comparing the sequence and size characteristics of the cleavage fragment with a database contacting sequence and size characteristics of RNAs associated with known genes.

4. A method of claim 3 whereby said comparison is conducted by means of software operated on a microprocessor.

5. A system for identification and characterization of gene expression in one or more samples, comprised of:

(a) providing one or more samples comprising one or more mRNA molecules;

(b) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a detectable marker at its 5' end;

(c) contacting said mRNA with said identimer such that the polyT portion of the identimer hybridizes to the polyA tail of the mRNA and the VNNN portion of the identimer hybridizes with portions of the mRNA immediately upstream of the polyA tail;

(d) reverse transcribing the mRNA to produce a first strand cDNA that includes the identimer;

(e) synthesizing a second DNA strand complementary to the first strand cDNA to form a duplex;

(f) cleaving the duplex with at least one sequence-specific cleaving agent to provide one or more duplex cleavage fragments;

(g) ligating an adaptamer comprising an RNA polymerase promoter site to one or more of said cleavage fragments; and (h) amplifying the one or more ligated cleavage fragments using the identimer to produce one or more amplified fragments comprising sequence complementary to a 3' end of the mRNA.

6. A method of claim 5, further comprising the identification and characterization of the cleavage fragments according to the presence of the marker, the sequences corresponding to the VNNN nucleotide sequence and the sequence associated with the sequence-specific cleaving agent, and the size of the fragment.

7. A method of claim 6, further comprising the identification of any gene associated with the cleavage fragments by comparing the sequence and size characteristics of the cleavage fragment with a database contacting sequence and size characteristics of RNAs associated with known genes.

8. A method of claim 7 whereby said comparison is conducted by means of software operated on a microprocessor.

9. A method for identification and characterization of gene expression in two or more samples, comprised of:

(a) providing a first sample comprising one or more mRNA molecules;

(b) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a first detectable marker at its 5' end;

(c) contacting said mRNA in the first sample with the identimer comprising said first detectable marker such that the polyT portion of the identimer hybridizes to the polyA tail of the mRNA and the VNx portion of the identimer hybridizes with portions of the mRNA immediately upstream of the polyA tail;

(d) providing a second sample comprising one or more mRNA molecules;

(e) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a second detectable marker at its 5' end;

(f) contacting said mRNA in the second sample with the identimer comprising said second detectable marker such that the polyT portion of the identimer hybridizes to the polyA tail of the mRNA and the VNx portion of the identimer hybridizes with portions of the mRNA immediately upstream of the polyA tail;

(g) reverse transcribing the mRNA in each sample to produce a first strand cDNA that includes the respective identimer;

(h) synthesizing a second DNA strand complementary to the first strand cDNA to form a duplex;

(i) cleaving the duplex with at least one sequence-specific cleaving agent to provide one or more duplex cleavage fragments;

(j) ligating an adaptamer comprising an RNA polymerase promoter site to one or more of said cleavage fragments; and (k) amplifying the one or more ligated cleavage fragments using the respective identimer to produce one or more amplified fragments comprising sequence complementary to a 3' end of the mRNA.

10. A method of claim 9, further comprising the identification and characterization of the cleavage fragments according to the presence of the marker, the sequences corresponding to the VNx nucleotide sequence and the sequence associated with the sequence-specific cleaving agent, and the size of the fragment.

11. A method of claim 10, further comprising the identification of any gene associated with the cleavage fragments by comparing the sequence and size characteristics of the cleavage fragment with a database contacting sequence and size characteristics of RNAs associated with known genes.

12. A method of claim 11 whereby said comparison is conducted by means of software operated on a microprocessor.

13. A method for identification and characterization of gene expression in two or more samples, comprised of:
(a) providing a first sample comprising one or more mRNA molecules;
(b) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a first detectable marker at its 5' end;
(c) contacting said mRNA in the first sample with the identimer comprising said first detectable marker such that the polyT portion of the identimer hybridizes to the polyA tail of the mRNA and the VNNN portion of the identimer hybridizes with portions of the mRNA immediately upstream of the polyA tail;
(d) providing a second sample comprising one or more mRNA molecules;
(e) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a second detectable marker at its 5' end;
(f) contacting said mRNA in the second sample with the identimer comprising said second detectable marker such that the polyT portion of the identimer hybridizes to the polyA tail of the mRNA and the VNx portion of the identimer hybridizes with portions of the mRNA immediately upstream of the polyA tail;
(g) reverse transcribing the mRNA in each sample to produce a first strand cDNA that includes the respective identimer;
(h) synthesizing a second DNA strand complementary to the first strand cDNA to form a duplex;
(i) cleaving the duplex with at least one sequence-specific cleaving agent to provide one or more duplex cleavage fragments;
(j) ligating an adaptamer comprising an RNA polymerase promoter site to one or more of said cleavage fragments; and
(k) amplifying the one or more ligated cleavage fragments using the respective identimer to produce one or more amplified fragments comprising sequence complementary to a 3' end of the mRNA.

14. A method of claim 13, further comprising the identification and characterization of the cleavage fragments according to the presence of the marker, the sequences corresponding to the VNNN nucleotide sequence and the sequence associated with the sequence-specific cleaving agent, and the size of the fragment.

15. A method of claim 14, further comprising the identification of any gene associated with the cleavage fragments by comparing the sequence and size characteristics of the cleavage fragment with a database contacting sequence and size characteristics of RNAs associated with known genes.

16. A method of claim 15 whereby said comparison is conducted by means of software operated on a microprocessor.

17. A method for identification and characterization of gene expression in one or more samples, comprised of:
(l) providing one or more samples comprising one or more mRNA molecules;
(m) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a detectable marker at its 5' end;
(n) contacting said mRNA with said identimer such that the polyT portion of the identimer hybridizes to the polyA tail of the mRNA and the VNx portion of the identimer hybridizes with portions of the mRNA immediately upstream of the polyA tail;
(o) reverse transcribing the mRNA to produce a first strand cDNA that includes the identimer;
(p) synthesizing a second DNA strand complementary to the first strand cDNA to form a duplex;
(q) cleaving the duplex with at least one sequence-specific cleaving agent to provide one or more duplex cleavage fragments;
(r) ligating an adaptamer comprising an RNA polymerase promoter site to one or more of said cleavage fragments;
(s) amplifying the one or more ligated cleavage fragments by means of in vitro transcription using one or more RNA polymerases to produce in vitro transcribed RNA;
(t) contacting said in vitro transcribed RNA with said identimer such that the polyT portion of the identimer hybridizes to the polyA tail of the in vitro transcribed RNA and the VNx portion of the identimer hybridizes with portions of the in vitro transcribed RNA immediately upstream of the polyA tail; and
(u) reverse transcribing the in vitro transcribed RNA to produce a first strand cDNA that includes the identimer.

18. A method of claim 17, further comprising the identification and characterization of the cleavage fragments represented by the first strand cDNA according to the presence of the marker, the sequences corresponding to the VNx nucleotide sequence and the sequence associated with the sequence-specific cleaving agent, and the size of the fragment.

19. A method of claim 18, further comprising the identification of any gene associated with the cleavage fragments by comparing the sequence and size characteristics of the cleavage fragment with a database contacting sequence and size characteristics of RNAs associated with known genes.

20. A method of claim 19 whereby said comparison is conducted by means of software operated on a microprocessor.

21. A method for identification and characterization of gene expression in one or more samples, comprised of:
(a) providing one or more samples comprising one or more mRNA molecules;
(i) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a detectable marker at its 5' end;

(j) contacting said mRNA with said identimer such that the polyT portion of the identimer hybridizes to the polyA tail of the mRNA and the VNNN portion of the identimer hybridizes with portions of the mRNA immediately upstream of the polyA tail;

(k) reverse transcribing the mRNA to produce a first strand cDNA that includes the identimer;

(l) synthesizing a second DNA strand complementary to the first strand cDNA to form a duplex;

(m) cleaving the duplex with at least one sequence-specific cleaving agent to provide one or more duplex cleavage fragments;

(n) ligating an adaptamer comprising an RNA polymerase promoter site to one or more of said cleavage fragments;

(o) amplifying the one or more ligated cleavage fragments by means of in vitro transcription using one or more RNA polymerases to produce in vitro transcribed RNA;

(p) contacting said in vitro transcribed RNA with said identimer such that the polyT portion of the identimer hybridizes to the polyA tail of the in vitro transcribed RNA and the VNx portion of the identimer hybridizes with portions of the in vitro transcribed RNA immediately upstream of the polyA tail; and (q) reverse transcribing the in vitro transcribed RNA to produce a first strand cDNA that includes the identimer.

22. A method of claim 21, further comprising the identification and characterization of the cleavage fragments represented by the first strand cDNA according to the presence of the marker, the sequences corresponding to the VNNN nucleotide sequence and the sequence associated with the sequence-specific cleaving agent, and the size of the fragment.

23. A method of claim 22, further comprising the identification of any gene associated with the cleavage fragments by comparing the sequence and size characteristics of the cleavage fragment with a database contacting sequence and size characteristics of RNAs associated with known genes.

24. A method of claim 23 whereby said comparison is conducted by means of software operated on a microprocessor.

25. A method for identification and characterization of gene expression in two or more samples, comprised of:

(a) providing a first sample comprising one or more mRNA molecules;

(b) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a first detectable marker at its 5' end;

(c) contacting said mRNA in the first sample with the identimer comprising said first detectable marker such that the polyT portion of the identimer hybridizes to the polyA tail of the mRNA and the VNx portion of the identimer hybridizes with portions of the mRNA immediately upstream of the polyA tail;

(d) providing a second sample comprising one or more mRNA molecules;

(e) providing an identimer comprising an oligo-dT primer of sequence, from 5' to 3' end, of Tn-VNx, where n is an integer 8 or greater but not more than 50 representing the number of T's, V equals a nucleotide A, C, or G but not T, each N equals a nucleotide A, C, G, or T, and x is an integer 3 or greater but not more than 10 representing the number of N nucleotides, said identimer also comprising a second detectable marker at its 5' end;

(f) contacting said mRNA in the second sample with the identimer comprising said second detectable marker such that the polyT portion of the identimer hybridizes to the polyA tail of the mRNA and the VNx portion of the identimer hybridizes with portions of the mRNA immediately upstream of the polyA tail;

(g) reverse transcribing the mRNA in each sample to produce a first strand cDNA that includes the respective identimer;

(h) synthesizing a second DNA strand complementary to the first strand cDNA to form a duplex;

(i) cleaving the duplex with at least one sequence-specific cleaving agent to provide one or more duplex cleavage fragments;

(j) ligating an adaptamer comprising an RNA polymerase promoter site to one or more of said cleavage fragments;

(k) amplifying the one or more ligated cleavage fragments by means of in vitro transcription using one or more RNA polymerases to produce in vitro transcribed RNA;

(l) contacting said in vitro transcribed RNA with said identimer such that the polyT portion of the identimer hybridizes to the polyA tail of the in vitro transcribed RNA and the VNx portion of the identimer hybridizes with portions of the in vitro transcribed RNA immediately upstream of the polyA tail; and (m) reverse transcribing the in vitro transcribed RNA to produce a first strand cDNA that includes the identimer.

26. A method of claim 25, further comprising the identification and characterization of the cleavage fragments represented by the first strand cDNA according to the presence of the marker, the sequences corresponding to the VNx nucleotide sequence and the sequence associated with the sequence-specific cleaving agent, and the size of the fragment.

27. A method of claim 26, further comprising the identification of any gene associated with the cleavage fragments by comparing the sequence and size characteristics of the cleavage fragment with a database contacting sequence and size characteristics of RNAs associated with known genes.

28. A method of claim 27 whereby said comparison is conducted by means of software operated on a microprocessor.

29. A method for identification and characterization of gene expression in two or more samples, comprised of:

(a) providing a first sample comprising one or more mRNA molecules;

(b) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a first detectable marker at its 5' end;

(c) contacting said mRNA in the first sample with the identimer comprising said first detectable marker such that the polyT portion of the identimer hybridizes to the polyA tail of the mRNA and the VNx portion of the identimer hybridizes with portions of the mRNA immediately upstream of the polyA tail;

(d) providing a second sample comprising one or more mRNA molecules;

(e) providing an identimer comprising an oligo-dT primer of sequence, from 5' to 3' end, of Tn-VNNN, where n is an integer 8 or greater but not more than 50 representing the number of T's, V equals a nucleotide A, C, or G but not T, and each N equals a nucleotide A, C, G, or T, said identimer also comprising a second detectable marker at its 5' end;

(f) contacting said mRNA in the second sample with the identimer comprising said second detectable marker such that the polyT portion of the identimer hybridizes to the polyA tail of the mRNA and the VNNN portion of the identimer hybridizes with portions of the mRNA immediately upstream of the polyA tail;

(g) reverse transcribing the mRNA in each sample to produce a first strand cDNA that includes the respective identimer;

(h) synthesizing a second DNA strand complementary to the first strand cDNA to form a duplex;

(i) cleaving the duplex with at least one sequence-specific cleaving agent to provide one or more duplex cleavage fragments;

(j) ligating an adaptamer comprising an RNA polymerase promoter site to one or more of said cleavage fragments;

(k) amplifying the one or more ligated cleavage fragments by means of in vitro transcription using one or more RNA polymerases to produce in vitro transcribed RNA;

(l) contacting said in vitro transcribed RNA with said identimer such that the polyT portion of the identimer hybridizes to the polyA tail of the in vitro transcribed RNA and the VNx portion of the identimer hybridizes with portions of the in vitro transcribed RNA immediately upstream of the polyA tail; and (m) reverse transcribing the in vitro transcribed RNA to produce a first strand cDNA that includes the identimer.

30. A method of claim 29, further comprising the identification and characterization of the cleavage fragments represented by the first strand cDNA according to the presence of the marker, the sequences corresponding to the VNNN base pair sequence and the sequence associated with the sequence-specific cleaving agent, and the size of the fragment.

31. A method of claim 30, further comprising the identification of any gene associated with the cleavage fragment by comparing the sequence and size characteristics of the cleavage fragments with a database contacting sequence and size characteristics of RNAs associated with known genes.

32. A method of claim 31 whereby said comparison is conducted by means of software operated on a microprocessor.

\* \* \* \* \*